US010729728B2

(12) United States Patent
Escaich Ferrer et al.

(10) Patent No.: US 10,729,728 B2
(45) Date of Patent: Aug. 4, 2020

(54) PROCESS FOR PREPARING AN ANIMAL BRAIN EXTRACT

(71) Applicant: BIOIBERICA, S.A., Barcelona (ES)

(72) Inventors: Josep Escaich Ferrer, Barcelona (ES); Daniel Martinez Puig, Vic (ES); Pere Dalmau Castañares, Palafolls (ES); Ramon Ruhi Roura, Barcelona (ES); Joaquima Guix Salichs, Sant Genis de Palafolls (ES); Josep Ribas Maynou, Palafolls (ES); Artur Alfocea Egüén, Sant Cugat del Valles (ES); Antonio Garcia Pedrosa, Lloret de Mar (ES); Purificación Morales García, Pineda de Mar (ES); Pere Leon Martín, Blanes (ES); Marta Badias Eroles, Barcelona (ES)

(73) Assignee: BIOIBERICA, S.A., Barcelona (ES)

( * ) Notice: Subject to any disclaimer, the term of this patent is extended or adjusted under 35 U.S.C. 154(b) by 0 days.

(21) Appl. No.: 15/575,626

(22) PCT Filed: Apr. 25, 2016

(86) PCT No.: PCT/EP2016/059121
§ 371 (c)(1),
(2) Date: Nov. 20, 2017

(87) PCT Pub. No.: WO2016/188684
PCT Pub. Date: Dec. 1, 2016

(65) Prior Publication Data
US 2018/0140638 A1 May 24, 2018

(30) Foreign Application Priority Data
May 22, 2015 (EP) .................................... 15382272

(51) Int. Cl.
*A61K 35/30* (2015.01)
*A61P 25/28* (2006.01)
*A61K 31/23* (2006.01)

(52) U.S. Cl.
CPC .............. *A61K 35/30* (2013.01); *A61K 31/23* (2013.01); *A61P 25/28* (2018.01)

(58) Field of Classification Search
CPC .......... A61P 25/28; A61K 35/30; A61K 31/23
See application file for complete search history.

(56) References Cited

U.S. PATENT DOCUMENTS 6,620,793 B2    9/2003   Toffano et al.

FOREIGN PATENT DOCUMENTS

| CN | 1813797 A | 8/2006 |
| EP | 0 150 712 A2 | 8/1985 |
| EP | 0 548 406 A1 | 6/1993 |
| EP | 2 309 854 A1 | 4/2011 |
| GB | 1 256 755 A | 12/1971 |
| JP | 10-016795 A | 1/1998 |
| WO | 2006/114790 A2 | 11/2006 |
| WO | 2010/007620 A1 | 1/2010 |

OTHER PUBLICATIONS

Folch et al. A simple method for the isolation and purification of total lipides from animal tissues. J Biol Chem. May 1957;226(1):497-509.*
Thannhauser et al. Isolation and identification of hydrolecithin (dipalmityl lecithin) from brain and spleen. J Biol Chem. Jan. 1948;172(1):135-9.*
Vickers, JC. A vaccine against Alzheimer's disease: developments to date. Drugs Aging 2002; 19(7):487-94.*
Hampel et al. The future of Alzheimer's disease: the next 10 years. Prog Neurobiol. Dec. 2011;95(4):718-28. Epub Nov. 22, 2011.*
Oertel, WH. Recent advances in treating Parkinson's disease. F1000Res. Mar. 13, 2017;6:260. doi: 10.12688/f1000research.10100.1. eCollection 2017.*
Insel, TR. Rethinking schizophrenia. Nature. Nov. 11, 2010;468(7321):187-93. doi: 10.1038/nature09552.*
Puzzo et al. Behavioral assays with mouse models of Alzheimer's disease: practical considerations and guidelines. Biochem Pharmacol. Apr. 15, 2014;88(4):450-67. Epub Jan. 21, 2014.*
R.S. Diaz, et al., "Preparation of a Protein-Free Total Brain White Matter Lipid Fraction: Characterization of Liposomes", Journal of Neuroscience Research, Jan. 1, 1992, pp. 136-145, vol. 31, No. 1.
International Search Report for PCT/EP2016/059121 dated Jun. 15, 2016 [PCT/ISA/210].
Written Opinion for PCT/EP2016/059121 dated Jun. 15, 2016 [PCT/ISA/237].

* cited by examiner

*Primary Examiner* — Gregory S Emch
(74) *Attorney, Agent, or Firm* — Hayes Soloway PC

(57) ABSTRACT

The present invention refers to a process for preparing an animal brain extract. It also refers to the brain extract obtainable according to said process and to the use thereof as a medicine, in particular for the prevention and/or treatment of neurodegenerative diseases and disorders of the central nervous system. It also refers to compositions comprising this extract and to its use for preparing these compositions.

22 Claims, 5 Drawing Sheets

Figure 1:
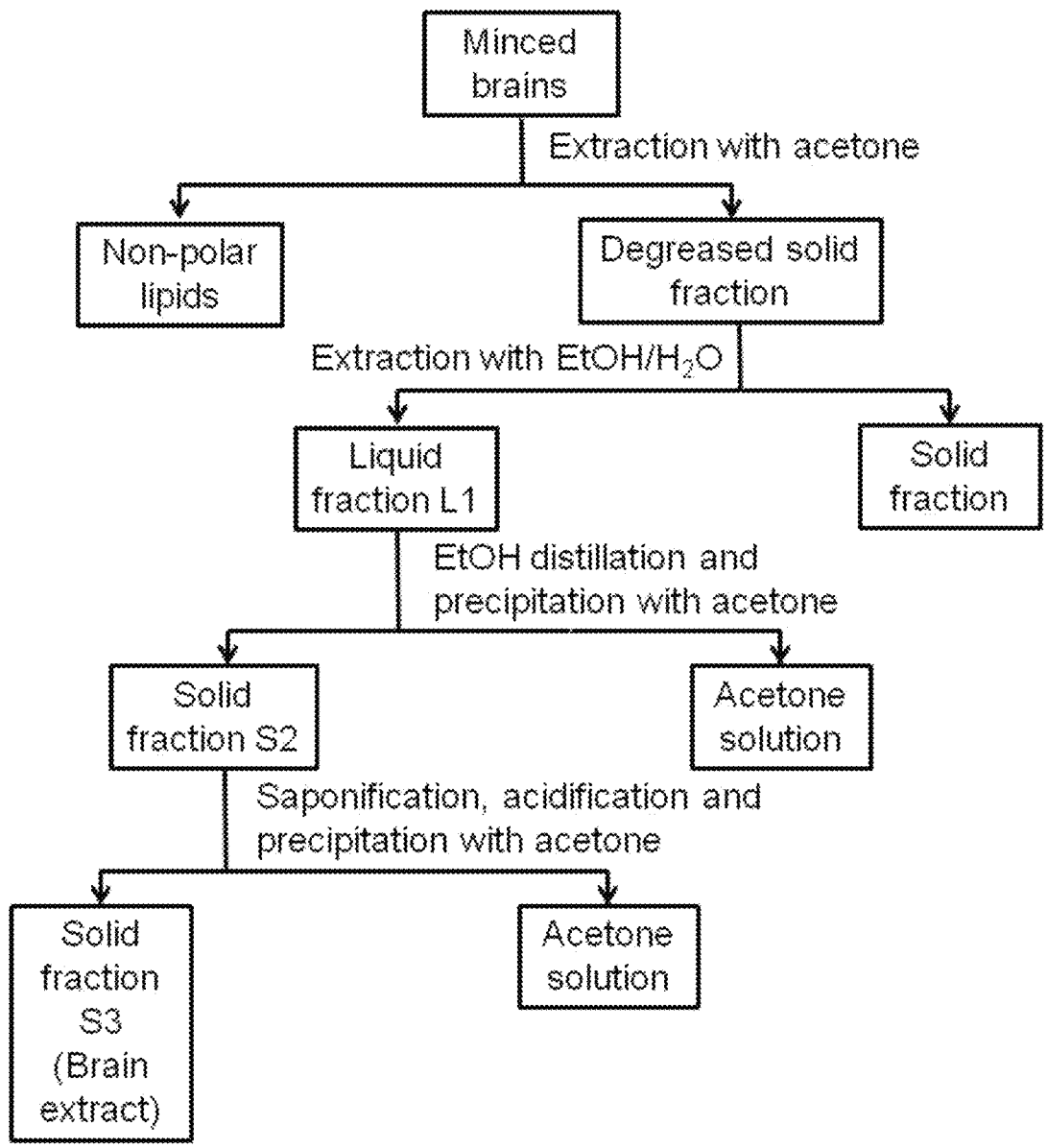

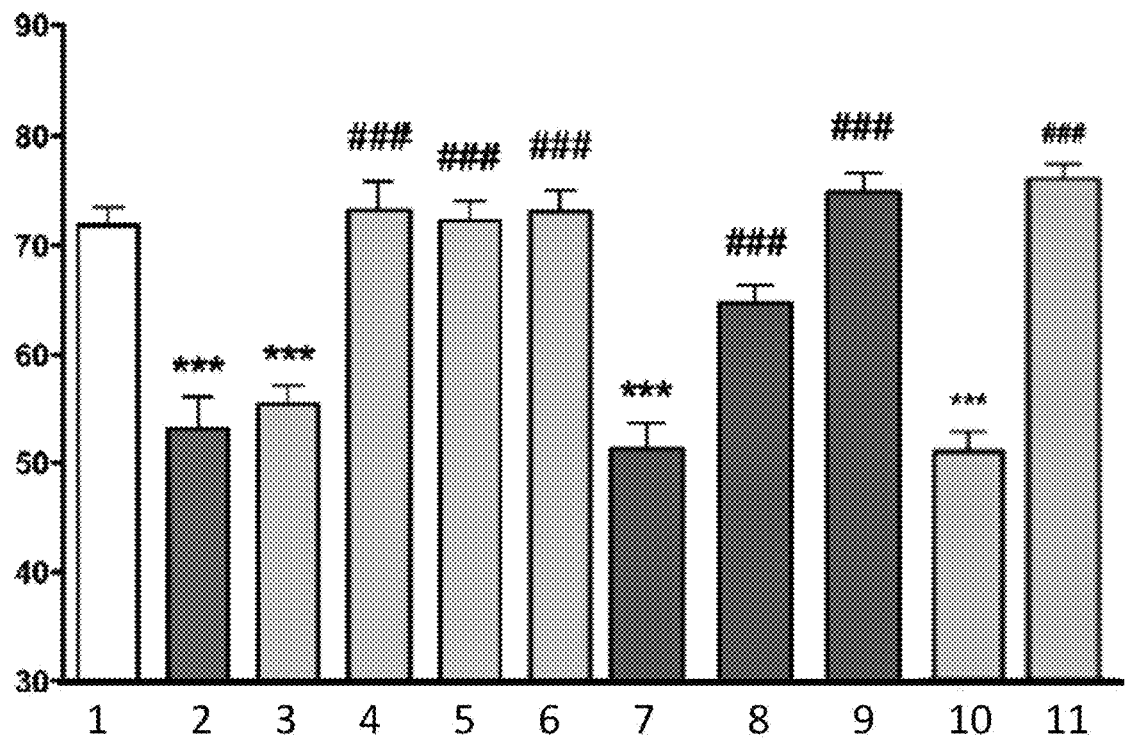
Figure 2.1
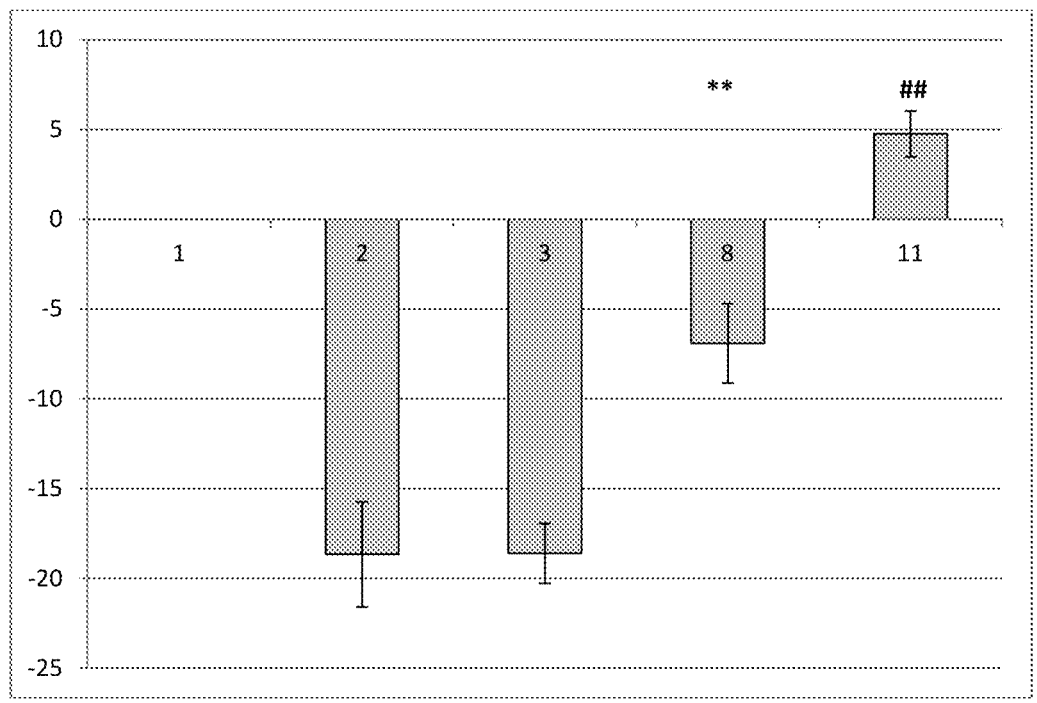
Figure 2.2

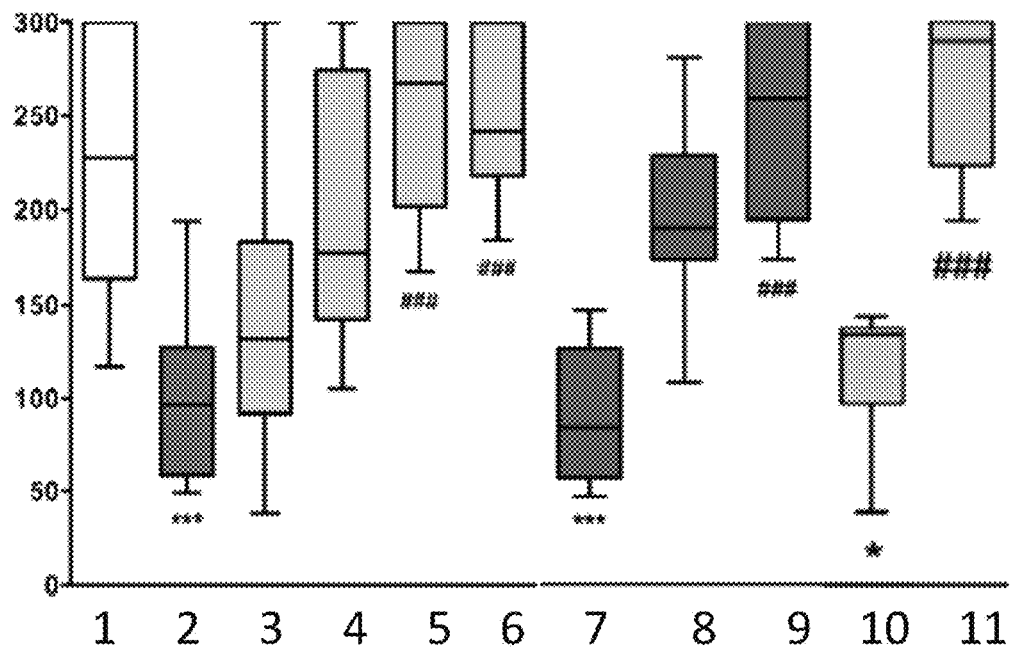
Fiigure 3.1
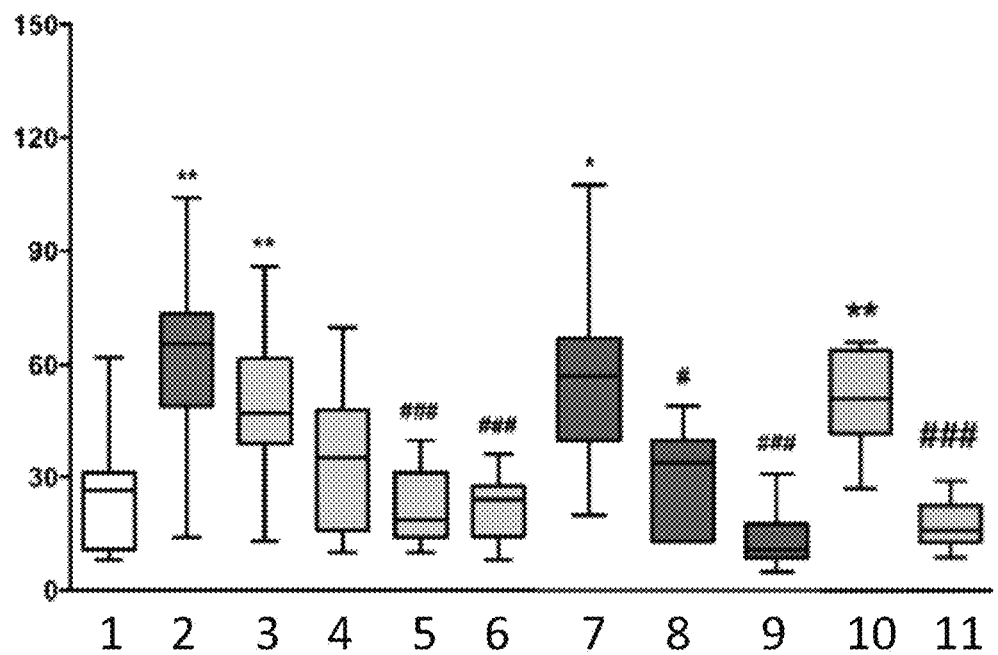
Figure 3.2

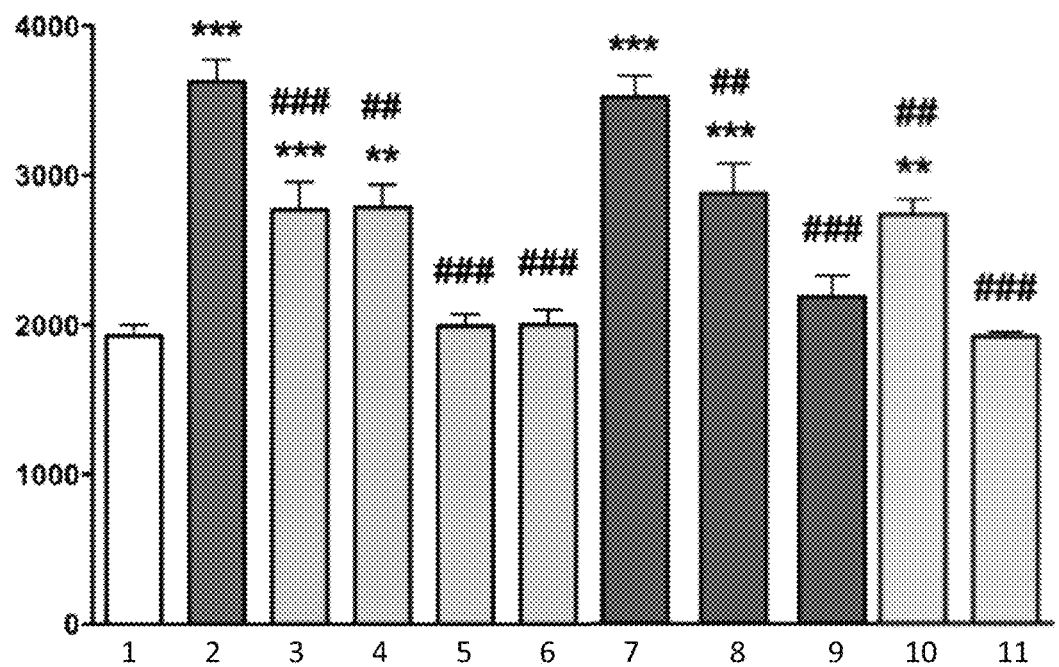
Figure 4
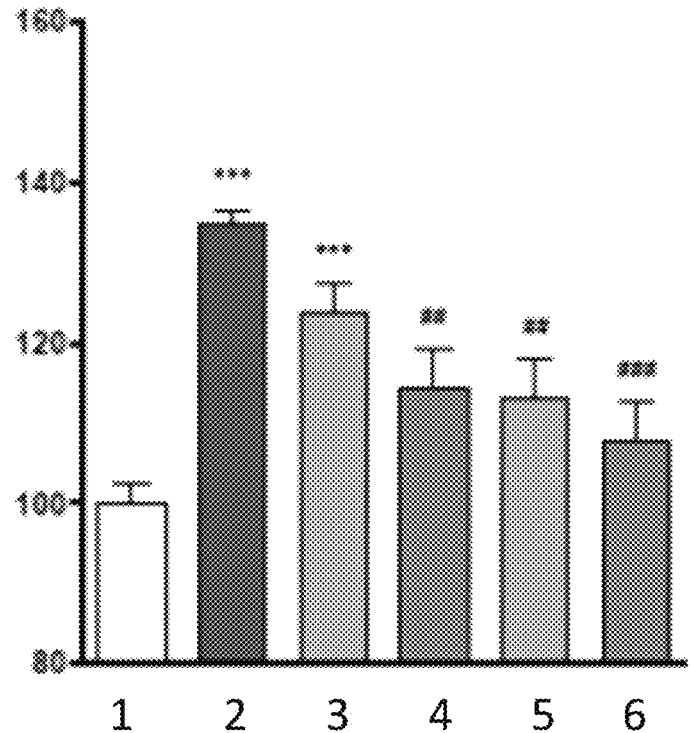
Figure 5.1

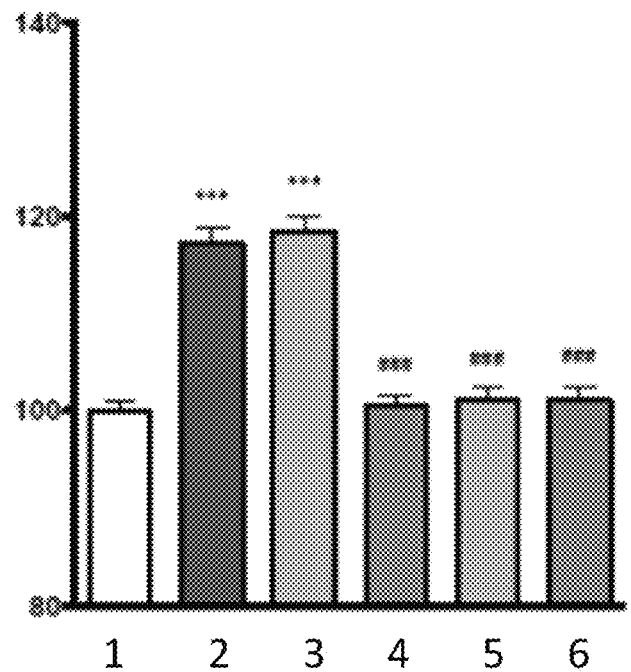
Figure 5.2
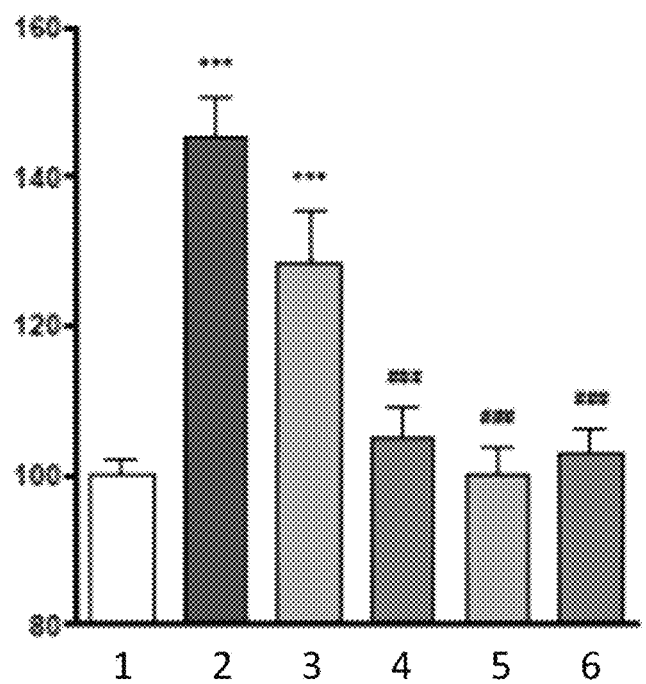
Figure 5.3

PROCESS FOR PREPARING AN ANIMAL BRAIN EXTRACT

CROSS REFERENCE TO RELATED APPLICATIONS

This application is a National Stage of International Application No. PCT/EP2016/059121 filed Apr. 25, 2016, claiming priority based on European Patent Application No. 15382272.1 filed May 22, 2015, the contents of all of which are incorporated herein by reference in their entirety.

TECHNICAL FIELD

The present invention belongs to the field of the preparation of extracts from biological materials and the use thereof in the prevention and/or treatment of neurodegenerative diseases and disorders of the central nervous system.

STATE OF THE ART

Neurodegenerative diseases are a group of diseases of unknown cause which affect the nervous system, and whose common characteristic is the progressive course of symptoms, reflecting the gradual disintegration of a part or parts of the nervous system. Among the neurodegenerative diseases affecting people, are Alzheimer's disease, Friedreich's ataxia, epilepsy, amyotrophic lateral sclerosis, spinal muscular atrophy, Parkinson's disease, Huntington's disease, or stroke.

Neurodegenerative diseases do not have an etiological treatment and the therapeutic interventions are symptomatic in some cases and palliative in all of them. They cause disability and a high physical and psychological suffering among their sufferers and among their families.

The socio-economic repercussions are very important, since to the disease process itself, it must be added the psychological impact, the loss of the quality of life, working incapacity, the loss of social skills, the physical and mental burden of the caregivers of these patients and the high economic cost involved in the social and health care of all these people.

Some drugs have been described in the prior art to prevent and/or treat such diseases. For example, for the treatment of mild to moderate symptoms of Alzheimer's disease cholesterase inhibitors are used, such as galantamine, rivastigmine and donepezil, and for the treatment of moderate to severe symptoms of this disease memantine is used, which is an antagonist of the N-methyl-D-aspartate. These medications can cause side effects such as dizziness, headaches, constipation, nausea, vomiting, weight loss, or muscle weakness.

It has also been described the use of nutraceutical and dietary compositions comprising neurological components as adjuvants for the prevention and/or treatment of neurodegenerative diseases, or to support the health of the nervous system. Among the neurological components are, for example, glycerophospholipids as phosphatidylcholine (PC), phosphatidylserine (PS), phosphatidylethanolamine (PE), phosphatidylinositol (PI); sphingophospholipids such as sphingomyelins and ceramides; sphingoglycolipids such as gangliosides, cerebrosides and sulfatides.

In this regard, different processes have been described for obtaining such neurological components with different degrees of purity or as mixtures thereof from biological materials such as, for example, organs from various animals, milk, nuts, cereals or fungi.

In the British patent GB1256755 an extract of brain mitochondria is described, which is suitable for the treatment or prevention of brain disorders, especially those affecting to the degree of consciousness and cerebral oedema. The extract is obtained by a sequence of centrifugations at different speeds of a brain homogenized in an aqueous solution comprising mannitol and EDTA, and which is adjusted to a pH of 7.4.

In the Japanese patent application JP-A-1016795 bovine brain extracts are described prepared from the extraction with aqueous ammonium sulphate. With this process, protein, phospholipid and sphingolipid fractions are obtained. In the Russian patent application RU-A-1994012010 a process for extracting nervone cerebroside from a porcine brain is described. The extraction is performed with acetone, the filtrate is precipitated with ethanol, and the final product is purified by washing with acetone.

In the Chinese patent application CN-A-85102590 a process for obtaining an extract of brain gangliosides is described, in which an adsorbent resin is used to separate the active product. In the Chinese patent application CN-A-1522752 it is disclosed the use of this extract for treating neurological disorders of the brain. In the Chinese patent application CN-A-1596733 a process for preparing an extract of bovine or porcine brain is described, which comprises the grinding of the brains, the treatment thereof with a combination of enzymes, hydrolysis with hydrochloric acid, neutralization and lyophilisation. According to the description, this extract is suitable for improving the nutritional status of the body and the regulation of brain functioning.

In the Chinese patent application CN-A-1771992 it is disclosed an extract of brain of a mammal comprising polypeptides, lysine, glutamic acid, and sugar. According to the description, the extract is suitable for regulating and improving brain metabolism as well as for treating vascular diseases.

In the Spanish patent ES540861 a method for extracting gangliosides is described comprising homogenizing the brain of a porcine, bovine or ovine animal in a solution of methanol and water in the presence of a surfactant, purification through a column, and a final desalination of the extract through a column.

In the international patent application WO-A-2010/007620 it is described a porcine brain extract which includes a mixture of peptides and proteins with a molecular weight of at least 5000 Da. It is also described its use as protector of muscle cells and neurons against hypoxia and apoptosis.

In the article Jittiwat et al., *Porcine Brain Extract Attenuates Memory Impairments Induced by Focal Cerebral Ischemia*, Am. J. Applied Sci., 2009, 6(9), 1662-1668, a porcine brain extract is described, comprising a mixture of the aminoacids aspartic acid and glutamic acid, and its use as neuroprotective. In the article Thukham-Mee et al., *Neuroprotective Effect against Alzheimer's Disease of Porcine Brain Extract*, Am. J. Applied Sci., 2012, 9(5), 700-708, is disclosed the use of the same extract as dietary supplement or adjuvant against Alzheimer's disease and other cognitive impairments due to aging.

In the international patent application WO-A-2006/114790 polar lipid mixtures are disclosed, which are obtained from materials different from brain. These mixtures contain PC, PE, PS, PI, and sphingophospholipids such as sphingomyelin, and the use thereof as food supplement is described.

In the European patent application EP-A-2309854 a process for preparing high-purity sphingomyelin is described, comprising the extraction of the total lipid fraction from a biological material with a mixture of an aliphatic hydrocarbon and a hydrosoluble ketone to obtain an insoluble fraction containing sphingomyelin, which is purified by treatment with a phospholipase.

Lipid extracts obtained from different natural sources, both plant and animal, are also commercially available.

The company Avanti Polar Lipids, Inc. commercializes, among other products, various natural extracts from egg, heart, brain, liver, soy, yeast, and *E. coli*. Among them there is a complete lipid brain extract, which is obtained by extraction with a mixture of chloroform and methanol, and that contains 26% by weight of PC, 10.6% by weight of PS, 1.6% by weight of PI, 16.7% by weight of PE, 2.8% by weight of phosphatidic acid, and 58.7% by weight of unidentified compounds. Also an extract of polar lipids from brain, which is obtained from the complete lipid extract by precipitation with acetone, and extraction of the precipitate obtained with dimethyl ether. According to the technical information, it contains a 12.6% by weight of PC, 18.5% by weight of PS, 33.1% by weight of PE, 4.1% by weight of PI, 0.8% by weight of phosphatidic acid and 30.9% by weight of unidentified compounds.

Notwithstanding the solutions disclosed in the prior art, it remains the need for providing a new process, easily implementable on an industrial scale, to prepare extracts with specific combinations of neurological components to be used in the prevention and/or treatment of neurodegenerative diseases and to support the health of nervous system.

OBJECT OF THE INVENTION

The object of the present invention is a process for preparing an animal brain extract.

Another aspect of the invention is a brain extract obtainable according to said process.

Another aspect of the invention is a composition comprising this extract.

Another aspect of the invention is this extract for use as a medicament.

Another aspect of the invention is the use of this extract for the preparation of compositions.

FIGURES

FIG. 1

In FIG. 1 a scheme of a preferred embodiment of the process of the invention is shown.

FIG. 2

In FIG. 2.1 the results corresponding to the spontaneous alternation in the Y-maze test displayed in TABLE V of the Example 3A are shown. With this test the spatial working memory is assessed. In the abscissa are the treatment groups, and in the ordinates is represented the percentage of alternation mean value (***$p<0.001$ vs. control group treated with vehicle and Sc.Aβ; ### $p<0.001$ vs. the group treated with vehicle and $Aβ_{25-35}$; Dunnett's test).

In FIG. 2.2 the results corresponding to the spontaneous alternation in the Y-maze test displayed in TABLE VI of the Example 3A are shown. With this test the spatial working memory is assessed. In the abscissa are the treatment groups, and in the ordinates is represented the average value of the difference vis-à-vis the control group treated with vehicle and Sc.Aβ (group 1) of the percentage of alternation for the group treated with vehicle and $Aβ_{25-35}$ (group 2), the group treated with the extract of the invention (group 3), the group treated with an extract comprising DHA (group 8), and the group treated with the extract of the invention and the extract comprising DHA (group 11). Differences between groups 2 and 3 are not significant, while groups 8 and 11 are significantly different from each other and vis-à-vis the other two groups (**$p<0.01$ vs. the group treated with vehicle and $Aβ_{25-35}$; ## $p<0.01$ vs. the group treated with vehicle and $Aβ_{25-35}$ and with the group 8; Tukey test).

FIG. 3

In FIG. 3 the results corresponding to the passive avoidance test displayed in TABLE VIII of Example 3A are shown. With this test the contextual long-term memory is assessed. In the abscissa are the treatment groups, and in the ordinates is the mean value of the step-through latency time (FIG. 3.1) and the escape latency time (FIG. 3.2), both expressed in seconds (*$p<0.05$; $p<0.01$, *$p<0.001$ vs. the control group treated with vehicle and Sc.Aβ; # $p<0.05$, ### $p<0.001$ vs. the group treated with vehicle and $Aβ_{25-35}$; Dunnett's test).

FIG. 4

In FIG. 4 the results corresponding to the lipid peroxidation assay displayed in TABLE IX of the Example 3A are shown. In the ordinates are represented the treatment groups and in the abscissa the mean value of CHP equivalents per weight of wet tissue (ECHP) ($p<0.01$, *$p<0.001$ vs. the control group treated with vehicle and Sc.Aβ; ## $p<0.01$, ### $p<0.001$ vs. the group treated with vehicle and $Aβ_{25-35}$; Dunnett's test).

FIG. 5

In FIG. 5 the results corresponding to the proinflammatory cytokines assay displayed in TABLE XI of the Example 3B are shown. In the ordinates are represented the treatment groups, and in the abscissa the mean value expressed in pg/ml for each of the cytokines IL1β (FIG. 5.1), IL6 (FIG. 5.2) and TNFα (FIG. 5.3) (***$p<0.001$ vs. the control group treated with vehicle and Sc.Aβ; ## $p<0.01$, ### $p<0.001$ vs. the group treated with vehicle and $Aβ_{25-35}$; Dunnett's test). The result of control group 1 is taken as base 100, and the other groups are referred to it.

DETAILED DESCRIPTION OF THE INVENTION

The object of the present invention is a process for preparing an animal brain extract comprising:

1) subjecting minced brains to an extraction with a mixture of ethanol:water or with a mixture of chloroform:methanol and separating the liquid fraction, referred to as L1, 2) distilling the solvent of the liquid fraction L1, and precipitating with acetone to obtain the solid fraction, referred to as S2, 3) saponifying the solid fraction S2, discarding the products soluble in acetone resulting from the saponification, and obtaining the solid fraction, referred to as S3.

The authors of the present invention have developed a new process for preparing a brain extract, in particular from a porcine animal, which stands out for its simplicity and ease for industrial implementation. This extract is suitable for the prevention and/or treatment of neurodegenerative diseases and disorders of the central nervous system, since it is able to prevent the deficits of the working memory and of the long-term memory, and also provides neuroprotective activity as it reduces the levels of lipid peroxidation and proinflammatory cytokines.

In the present description, as well as in the claims, the singular forms "a", "an", "one" or "the" include the plural reference unless the context clearly indicates otherwise.

In the context of the invention, the term "non-polar lipids" refers to those lipid compounds insoluble in water and soluble in acetone, such as, for example, cholesterol.

In the context of the invention, the term "complex polar lipids" refers to lipid compounds that include in their structure an amide bond with a fatty acid moiety, such as, for example, sphingomyelins, gangliosides, ceramides, and sulfatides.

In the context of the invention, the term "phospholipid" refers to those lipid compounds that include in their structure the phosphated glycerin and fatty acid moieties linked by ester groups, for example, phosphatidylcholine, phosphatidylserine, phosphatidylinositol, phosphatidylethanolamine.

Process

The process of the invention for preparing the animal brain extract is a simple process which allows obtaining an extract having a specific profile of complex polar lipids which provides it with remarkable neuroprotective properties, as discussed below.

In the process of the invention brains from mammals are employed as raw material, preferably of porcine, bovine or ovine origin, and more preferably of porcine origin.

In the process of the invention minced brains are used. The brains can be triturated by methods well known to the skilled man.

Extraction of Complex Polar Lipids and Phospholipids

In the process of the invention an extraction of the minced brains is performed by employing an ethanol:water mixture, generally in a ratio comprised between 80:20 and 60:40 expressed by (v/v), preferably between 75:25 and 65:35, and more preferably 70:30. Alternatively, the extraction is carried out by using a chloroform:methanol mixture in a ratio comprised between 70:30 and 60:40, more preferably between 68:42 and 65:45, and more preferably 66:33. Said extraction generally is performed under stirring at a temperature comprised between 40° C. and 70° C., preferably between 50° C. and 65° C., and more preferably between 55° C. and 60° C., for a minimum time of 4 h, preferably for a minimum of 6 h, and more preferably for a minimum of 8 h. In this extraction the solid residue is discarded, and the process of the invention continues with the liquid fraction, which is referred to as L1.

This extraction process with the mixture of ethanol:water or chloroform:methanol can be repeated several times. In this case, the supernatants from the several extractions are pooled before continuing with the process. Preferably said extraction is performed at least twice.

The process of the invention continues with the liquid fraction L1.

Extraction of Non-Polar Lipids

In a preferred embodiment, the process of the invention comprises a previous step of degreasing of the brains by extraction with a solvent selected from acetone, hexane, and a supercritical fluid such as carbonic anhydride in supercritical conditions. Preferably acetone is used.

In said step, brains are degreased prior to the extraction with the mixture of ethanol:water or chloroform:methanol, by means of an extraction of the minced brains with one of the above-mentioned solvents. Such extraction allows the substantial removal of cholesterol and non-polar lipids.

The process of the invention preferably comprises a step consisting in subjecting the minced brains to an extraction with acetone. After such extraction, the liquid fraction, which substantially comprises cholesterol and non-polar lipids, is discarded, and the process of the invention continues with the degreased solid fraction.

Within the context of the invention, the substantial removal of cholesterol means that the content of it does not exceed 10% by weight relative to the dry weight of the minced and degreased brains, preferably 5%, and more preferably 1%.

Usually the extraction of the minced brains with the solvent is repeated several times until the water content of the liquid phase is less than 5% by weight.

The minced and degreased brains are drained and dried, generally under vacuum at a temperature comprised between 30° C. and 80° C., preferably between 40° C. and 70° C., more preferably between 50° C. and 65° C., and still more preferably at 60° C.

In this way, the degreased solid fraction is obtained as a powdery product which is incorporated into the process of the invention.

Distillation of the Solvent and Precipitation with Acetone

The process of the invention comprises distilling the solvent or solvents of the liquid fraction L1, and precipitation with acetone to obtain the solid fraction S2.

The solvent comes from the extraction carried out in the step of the process of the invention by employing ethanol:water or chloroform:methanol.

The distillation of the solvent or solvents may be accomplished by processes well known to the skilled in the art, for example, under vacuum and at a temperature comprised between 50° C. and 65° C., preferably at 60° C.

In the precipitation with acetone, a volume of acetone of from 3 to 5 times is generally used, and preferably 4 times.

The addition of acetone to the aqueous solution obtained after the distillation of ethanol, results in the precipitation of the complex polar lipids and phospholipids in form of solid fraction S4. After decantation and removal of the liquid fraction, the solid obtained can be washed with acetone repeated times. Generally, 2-4 volumes of acetone are employed over the solid, preferably 3 volumes, and it is kept under stirring for a time approximately comprised between 20 min and 1 h, preferably 30 min, at room temperature. In each wash with acetone, the supernatant is discarded and solid fraction containing the complex polar lipids and phospholipids is kept. Preferably, said solid fraction is dried under vacuum at a temperature comprised between 30° C. and 80° C., preferably between 40° C. and 70° C., more preferably between 50° C. and 65° C., and still more preferably at 60° C. Thus, a solid is obtained in form of powdery product, referred to as solid fraction S2, which is subjected to saponification.

The process of the invention continues with the solid fraction S2, preferably dried.

Saponification

The solid fraction S2 is saponified. Preferably, the saponification is carried out with this fraction suspended in water.

The result of the saponification of the solid fraction S2 is a mixture comprising the complex polar lipids, which substantially constitute the extract of the invention, and also the compounds from the saponification of the phospholipids which are found in said solid fraction, among them the fatty acids, possibly in the form of soaps.

The saponification of said solid fraction can be carried out by well known standard processes, such as, for example, by suspending said fraction in an aqueous solution of an alkali hydroxide, preferably sodium hydroxide or potassium hydroxide, more preferably potassium hydroxide, at a concentration comprised between 0.3 M and 3 M, more preferably between 0.4 M and 1 M, and more preferably 0.5 M, at a temperature comprised between 30° C. and 80° C., preferably between 40° C. and 70° C., more preferably between 50° C. and 65° C., and still more preferably at 60° C., and for a period of time comprised between 3 h and 12 h, preferably between 5 h and 10 h, more preferably between 7 h and 9 h, and still more preferably 8 h. The saponification of this fraction may also be carried out by using enzymes, such as lipases. In this case, the saponification is preferably carried out at a temperature comprised between 50° C. and 60° C., preferably at 55° C., and at a pH comprised between 5.5 and 6.5, preferably at pH 6.

Preferably, the saponification is carried out by treatment with an aqueous solution of an alkali hydroxide.

Once the solid fraction S2 is saponified, the process continues with the isolation of the extract of the invention.

Isolation of the Brain Extract

The isolation of the brain extract of the invention from the saponification reaction mixture can be carried out by standard methods well known to the skilled in the art. For example, it may be isolated by acidifying the reaction mixture obtained after saponification, precipitation with acetone, and separation of the solid obtained, referred to as solid fraction S3, which is the extract object of the invention.

The acidification can be performed by using a mineral acid, such as concentrated hydrochloric acid, to a pH value comprised between 1 and 3, preferably 2.

The precipitation with acetone is carried out over the acid suspension obtained after acidification. Usually, to precipitate the complex polar lipids acetone is added in a proportion of 3 to 5 volumes of acetone relative to the volume of the acid suspension, preferably 4 volumes.

After the precipitation with acetone, the mixture obtained can be decanted to discard the supernatant, comprising the compounds from the saponification of phospholipids, including fatty acids. After decantation and removal of the liquid fraction, the solid obtained can be washed with acetone repeated times. Generally, 2-4 volumes of acetone are employed over the solid, preferably 3 volumes, and is kept under stirring for a time approximately comprised between 20 minutes and 1 hour, preferably 30 minutes, at room temperature. In each wash with acetone the supernatant is discarded and solid fraction containing the complex polar lipids, which substantially constitute the extract of the invention, is retained.

The process of the invention preferably further comprises a washing step to remove the salts which are in the solid fraction S3, in case that the saponification has been carried out with an alkali hydroxide. This step is not necessary in case of using an enzymatic saponification.

The removal of salts from said solid fraction can be performed by washing said solid fraction with a mixture of ethanol:water or acetone:water in a ratio of 80:20 (v/v) between the two solvents, until the concentration of the anion from the acid used in the acidification is less than 1%, in the case that hydrochloric acid has been employed as acidifying agent in step 5) the washing is continued until the chloride ion concentration is less than 1%.

After the possible removal of salts, the process of the invention preferably includes a drying step of the washed solid fraction. This drying step is generally carried out under vacuum at a temperature comprised between 30° C. and 80° C., preferably between 40° C. and 70° C., more preferably between 50° C. and 65° C., and still more preferably at 60° C.

In this way, a brain extract is obtained having a composition with a content of phospholipids and triacylglycerides lower than 10%, preferably lower than 6%, and more preferably lower than 1%, and which is substantially constituted by complex polar lipids as sphingomyelins, gangliosides, ceramides and sulfatides.

The content of sphingomyelins is generally comprised between 28% and 43% by weight relative to the total weight of the extract. Within the group of sphingomyelins, dihydrosphingomyelins are also included. The content of gangliosides is generally comprised between 34% and 46% by weight relative to the total weight of the extract. Within the group of gangliosides the following gangliosides are included: GM1 (monosialotetrahexosylganglioside), GM2, GM3 (monosialodihexosylganglioside) and GD1. The content of ceramides is generally comprised between 12% and 19% by weight relative to the total weight of the extract. Within the group of ceramides the following are included: ceramides, dihydroceramides, glucosylceramides, and lactosylceramides. The content of sulfatides is generally comprised between 2% and 8% by weight relative to the total weight of the extract. The extract contains a low percentage of phospholipids (e.g. phosphatidylcholines, phosphatidylcholine-plasmalogens, and plasmalogens of lysophosphatidylethanol) and triacylglycerides, which is usually lower than 10%, preferably lower than 6%, and more preferably lower than 1% by weight relative to the total weight of the extract. The sum of the percentages of the components of the extract is the 100%.

In a preferred embodiment, the extract of the invention is obtained by a process comprising a saponification step which is performed by treatment with an aqueous solution of an alkali hydroxide. In this preferred embodiment, the extract has a content of sphingomyelins comprised between 30% and 43% by weight relative to the total weight of the extract, preferably between 32% and 40%, and more preferably between 33% and 39%. Within the group of sphingomyelins, dihydrosphingomyelins are also included. The content of gangliosides is comprised between 36% and 46% by weight relative to the total weight of the extract, preferably between 38% and 44%, and more preferably between 39% and 43%. Within the group of gangliosides the following gangliosides are included: GM1 (monosialotetrahexosylganglioside), GM2, GM3 (monosialodihexosylganglioside) and GD1. The content of ceramides is generally comprised between 13% and 19% by weight relative to the total weight of the extract, preferably between 14% and 18%, and more preferably between 15 and 17%. Within the group of ceramides the following are included: ceramides, dihydroceramides, glucosylceramides, and lactosylceramides. The content of sulfatides is generally comprised between 2% and 8% by weight relative to the total weight of the extract, preferably between 3% and 7%, and more preferably between 4% and 6.5%. The extract contains a low percentage of phospholipids (e.g. phosphatidylcholines, phosphatidylcholine-plasmalogens, and plasmalogens of lysophosphatidylethanol) and triacylglycerides, which is usually lower than 3%, preferably lower than 2%, and more preferably lower than 1% by weight relative to the total weight of the extract. The sum of the percentages of the components of the extract is the 100%.

In another embodiment, the extract of the invention is obtained by a process comprising a saponification step which is performed by enzymatic treatment. In this preferred embodiment, the extract has a content of sphingomyelins comprised between 28% and 41% by weight relative to the total weight of the extract, preferably between 32% and 39%, and more preferably between 33% and 37%. Within the group of sphingomyelins, dihydrosphingomyelins are also included. The content of gangliosides is comprised between 34% and 44% by weight relative to the total weight of the extract, preferably between 36% and 42%, and more preferably between 39% and 41%. Within the group of gangliosides the following gangliosides are included: GM1 (monosialotetrahexosylganglioside), GM2, GM3 (monosialodihexosylganglioside) and GD1. The content of ceramides is generally comprised between 12% and 18% by weight relative to the total weight of the extract, preferably between 14% and 17%, and more preferably between 15 and 16%. Within the group of ceramides the following are included: ceramides, dihydroceramides, glucosylceramides, and lactosylceramides. The content of sulfatides is generally comprised between 2% and 7% by weight relative to the total weight of the extract, preferably between 3% and 6%, and more preferably between 4% and 5%. The extract contains a low percentage of phospholipids (e.g. phosphatidylcholines, phosphatidylcholine-plasmalogens, and plasmalogens of lysophosphatidylethanol) and triacylglycerides, which is usually lower than 10%, preferably lower than 8%, and more preferably lower than 6% by weight relative to the total weight of the extract. The sum of the percentages of the components of the extract is the 100%.

Another aspect of the invention is a brain extract obtainable according to the process of the invention. Preferably the extract is obtainable according to the process of the invention that includes a saponification step with an alkali hydroxide.

Composition

Another aspect of the invention is a composition comprising the extract of the invention and at least one vehicle or excipient.

The composition of the invention may be a pharmaceutical composition, a food preparation, a functional food preparation, or a food supplement.

A pharmaceutical composition is a composition comprising an active substance with pharmacological activity, in this case the extract of the invention, and at least one pharmaceutically acceptable excipient.

A food preparation is a composition intended for human consumption which is composed of a matrix such as milk, milk preparations, yogurt, cheese, juices, soups, cereals, pasta, breads, drinks or snacks.

A functional food preparation is a composition intended for human consumption comprising components that provide health benefits, for example, omega-3 acids, stanols, sterols, prebiotics, probiotics, antioxidants, vitamins and minerals. Within this group are also included those foods for special medical purposes, that is, specially processed or formulated foods intended for the dietary management of patients, including infants, under medical supervision, i.e. designed to meet all or part of the alimentary needs either of patients whose capacity to ingest, digest, absorb, metabolise or excrete ordinary food or certain nutrients or metabolites thereof is limited or poor, or is impaired, or of those patients who need other clinically-determined nutrients, whose dietary management cannot be achieved by only modifying the normal diet.

A food supplement is a food composition whose purpose is to supplement the normal diet and it consists in concentrated sources of nutrients or other substances with a nutritional or physiological effect, in simple or combined form, marketed as dose forms, namely capsules, tablets, pills and other similar forms, sachets of powders, ampoules of liquids, bottles with droppers, and other similar forms of liquids and powders which must be taken in small unitary portions; wherein among the nutrients are the following substances: vitamins, minerals, botanical extracts, or extracts from animal (terrestrial or marine) sources.

The vehicle or excipient which is included in the composition depends on the type of composition.

When it is a pharmaceutical composition or a food supplement, the composition includes a pharmaceutically acceptable vehicle or excipient, which may be selected from those described, for example, in the handbook R. C. Rowe et al, *Handbook of Pharmaceutical Excipients*, $4^{th}$ edition, Pharmaceutical Press, London, 2003 [ISBN: 0-85369-472-9]. The selection thereof depends on the type of pharmaceutical composition to be prepared. The preparation of the different types of pharmaceutical dosage forms is well known to the skilled in the art and a description is available, for example, in the handbook *Remington The Science and Practice of Pharmacy*, $20^{th}$ edition, Lippincott Williams & Wilkins, Philadelphia, 2000 [ISBN: 0-683-306472].

Preferably, the composition of the invention comprises at least one additional active component suitable for the prevention and/or treatment of neurodegenerative and/or central nervous system diseases, or to support the health of the nervous system. The additional active components may be selected, for example, from the group consisting of omega-3 acids, such as docosahexaenoic acid (DHA), eicosapentaenoic acid (EPA), extracts containing them, and mixtures thereof, in the form of acids or as triglycerides, selenium, genistein, vitamin C, vitamin E, vitamins of the B group, folate, or medium chain fatty acids.

More preferably, the composition of the invention comprises an extract of omega-3 acids in form of triglycerides comprising DHA and EPA. More preferably, said extract comprises between 40% and 60% by weight of DHA, still more preferably 50% by weight of DHA. In a particularly preferred embodiment, the composition comprises extract of omega-3 acids in form of triglycerides comprising 50% by weight of DHA, 20% of EPA and the acids linolenic acid (C18:3n3), stearidonic acid (C18:4n3), C20:4n3, C21:5n3 and n3 docosapentaenoic acid (C22:5n3).

Another aspect of the invention is the use of the brain extract for the preparation of a composition selected from the group consisting of a pharmaceutical composition, a food supplement, a food preparation and a functional food preparation.

Use of the Brain Extract

Another aspect of the invention is the brain extract obtainable according to the process of the invention for use as a medicament, preferably for the prevention and/or treatment of neurodegenerative and/or central nervous system diseases, and to support the health of the nervous system. Among the neurodegenerative diseases, preferably are dementia, Alzheimer's disease, vascular dementia, Friedreich's ataxia, epilepsy, amyotrophic lateral sclerosis, spinal muscular atrophy, Parkinson's disease, Huntington's disease, or stroke, more preferably Alzheimer's disease.

The brain extract of the invention can be administered orally or parenterally. The dose to be administered depends on the patient's weight, but, generally, the daily dose is comprised between 500 mg and 5 g.

The brain extract of the invention is obtained by means of a process which can be easily implemented on an industrial scale, without the need of lengthy and tedious purifications, and also has significant neuroprotective properties.

The tests performed in a mouse model with the brain extract of the invention, and which are set forth in the Examples section, support the conclusion that, surprisingly, the oral administration of this extract prevents the deficits in spatial working memory, as well as the deficits in the long-term memory, and it also has a neuroprotective activity by reducing the levels of lipid peroxidation in hippocampal tissues, a consequence of oxidative stress, and by reducing the levels of inflammatory cytokines. It was also observed that the different treatments had no effect on the weight gain of the animals. It is also observed that the combination of the extract of the invention with an extract comprising DHA and EPA has a synergistic effect in the spontaneous alternation tests, so that this combination may be appropriate to prevent spatial working memory deficits.

The invention comprises the following embodiments:

1.—Process for preparing an animal brain extract, characterized in that it comprises:

1) subjecting minced brains to an extraction with a mixture of ethanol:water or with a mixture of chloroform:methanol and separating the liquid fraction, referred to as L1, 2) distilling the solvent of the liquid fraction L1, and precipitating with acetone to obtain the solid fraction, referred to as S2, 3) saponifying the solid fraction S2, discarding the products soluble in acetone resulting from the saponification, and obtaining the solid fraction, referred to as S3.

2.—Process according to embodiment 1, characterized in that the brain is of porcine origin.

3.—Process according to embodiment 1 or 2, characterized in that the ethanol:water mixture is in a ratio comprised between 80:20 and 60:40 expressed in (v/v).

4.—Process according to embodiment 3, characterized in that the ethanol:water mixture is a ratio of 70:30 (v/v).

5.—Process according to embodiment 1 or 2, characterized in that the chloroform:methanol mixture is in a ratio comprised between 70:30 and 60:40 expressed in (v/v).

6.—Process according to embodiment 5, characterized in that the chloroform:methanol mixture is in a ratio 66:33 expressed in (v/v).

7.—Process according to any of embodiments 1 to 6, characterized in that it comprises a previous step of degreasing of the brains by extraction with a solvent selected from acetone, hexane and carbonic anhydride in supercritical conditions.

8.—Process according to embodiment 7, characterized in that the previous step of degreasing of the brains is carried with acetone.

9.—Process according to any of embodiments 1 to 8, characterized in that the saponification is carried out by treatment with an aqueous solution of an alkali hydroxide.

10.—Process according to embodiment 9, characterized in that it further comprises a step of washing the solid fraction S3.

11.—Process according to any of embodiments 1 to 10, characterized in that it further comprises a step of drying the solid fraction S3.

12.—Brain extract obtainable according to the process of any of embodiments 1 to 11.

13.—Extract according to embodiment 12, characterized in that the content of sphingomyelins is comprised between 28% and 43% by weight relative to the total weight of the extract, the content of gangliosides is comprised between 34% and 46% by weight relative to the total weight of the extract, the content of ceramides is comprised between 12% and 19% by weight relative to the total weight of the extract, the content of sulfatides is comprised between 2% and 8% by weight relative to the total weight of the extract, and the content of phospholipids and triacylglycerides is lower than 10%, and the sum of the percentages of the components of the extract is the 100%.

14.—Extract according to embodiment 12, characterized in that the content of sphingomyelins is comprised between 30% and 43% by weight relative to the total weight of the extract, the content of gangliosides is comprised between 36% and 46% by weight relative to the total weight of the extract, the content of ceramides is comprised between 13% and 19% by weight relative to the total weight of the extract, the content of sulfatides is comprised between 2% and 8% by weight relative to the total weight of the extract, and the content of phospholipids and triacylglycerides is lower than 3%, and the sum of the percentages of the components of the extract is the 100%.

15.—Extract according to embodiment 12, characterized in that the content of sphingomyelins is comprised between 28% and 41% by weight relative to the total weight of the extract, the content of gangliosides is comprised between 34% and 44% by weight relative to the total weight of the extract, the content of ceramides is comprised between 12% and 18% by weight relative to the total weight of the extract, the content of sulfatides is comprised between 2% and 7% by weight relative to the total weight of the extract, and the content of phospholipids and triacylglycerides is lower than 10%, and the sum of the percentages of the components of the extract is the 100%.

16.—Composition characterized in that it comprises the extract of any of embodiments 12 to 15 and at least one vehicle or excipient.

17.—Composition according to embodiment 16, characterized in that it is a pharmaceutical composition, a food preparation, a functional food preparation, or a food supplement.

18.—The composition according to embodiment 16 or 17, characterized in that it comprises at least one additional active component suitable for the prevention and/or treatment of neurodegenerative and/or central nervous system diseases, or to support the health of the nervous system.

19.—The composition according to embodiment 18, characterized in that the additional active component comprises an extract of omega-3 acids in the form of triglycerides.

20.—The composition according to embodiment 19, characterized in that the additional active component comprises DHA and EPA.

21.—Brain extract of any of embodiments 12 to 15 for use as medicament.

22.—Brain extract for use according to embodiment 21 for the prevention and/or treatment of neurodegenerative and/or central nervous system diseases, and to support the health of the nervous system.

23.—Brain extract for use according to embodiment 22 for the prevention and/or treatment of neurodegenerative diseases selected from the group consisting of dementia, Alzheimer's disease, vascular dementia, Friedreich's ataxia, epilepsy, amyotrophic lateral sclerosis, spinal muscular atrophy, Parkinson's disease, Huntington's disease, or stroke.

24.—Brain extract for use according to embodiment 23 for the prevention and/or treatment of Alzheimer's disease.

25.—Use of the brain extract according to any of embodiments 12 to 15 for preparing a pharmaceutical composition, a food preparation, a functional food preparation, or a food supplement.

Next, some examples are included to illustrate the present invention but they should not be considered as a limitation thereof.

EXAMPLES

Example 1: Process for Preparing the Extract with Alkaline Saponification

Frozen pig brains were minced and transferred to the reactor for degreasing. Acetone was added in the amount required to achieve a percentage of acetone higher than 90%. After one hour stirring at room temperature the suspension was allowed to stand for decanting. The supernatant was sucked out. This operation was repeated until the water content of the liquid phase was less than 5%. The product was drained and dried under vacuum at a temperature of 60° C. A powdery product was obtained (Degreased solid fraction).

The powdery product obtained in the previous step was resuspended in a solution of ethanol:water in a volume ratio 70:30 (v/v) and in a proportion 7:1 relative to the weight of solid. It was allowed to stir at a temperature comprised between 55° C. and 60° C. for a minimum period of 8 h. Subsequently, the stirring was stopped and it was allowed to stand for decanting. The supernatant liquid was separated by decantation and was sent to another reactor.

The solid remaining in the initial reactor was subjected to a second resuspension in the same proportion and it was allowed to stir again for at least 4 h at a temperature comprised between 55° C. and 60° C. Subsequently, the stirring was stopped and it was allowed to stand for decanting. The supernatant liquid was separated by decantation and was sent to the reactor containing the supernatant from the first extraction. The combined supernatants constituted the liquid fraction L1.

After distilling the ethanol, the aqueous solution was precipitated by adding, under stirring, 4 volumes of acetone relative to the initial volume. It was allowed to stand for decanting and the supernatant was removed. On the solid obtained, about 3 volumes of acetone were added to the solid and stirred for at least 30 min. It was decanted and the supernatant was removed again. The product was drained and dried under vacuum at a temperature of 60° C. Thus the solid fraction S2 was obtained.

The solid product obtained was resuspended in an aqueous solution of 0.5 M potassium hydroxide at a temperature of 60° C. for 8 h. The suspension was neutralized with concentrated hydrochloric acid to a pH value of 2.

The product was precipitated with 4 volumes of acetone relative to the initial volume. It was decanted and the supernatant, containing the fatty acids from the saponification of the extract, was removed.

About 3 volumes of acetone were added over the solid and stirred for at least 30 min. It was decanted and the supernatant was removed. The solid fraction S3 was obtained.

Washes were carried out with a solution of ethanol:water in a rate 80:20 (v/v) until the chloride concentration in the supernatant was lower than 1%. The product was drained and dried under vacuum at a temperature of approximately 60° C.

The product was analyzed by HPLC, using a method based on the method described in Castro-Perez et al., *Comprehensive LC-MS E lipidomic analysis using a shotgun approach and its application to biomarker detection and identification in osteoarthritis patients*, J. Proteome Res., 2010, 9(5), 2377-89 (doi: 10.1021/pr901094j). Erratum in: J. Proteome Res., 2011, 10(7), 3303-8. The composition of the extract obtained in different batches expressed in % by weight is shown in Table I:

TABLE I

| Component | Batch 1 | Batch 2 |
|---|---|---|
| Ceramides | 3.9 | 3.5 |
| Dihydroceramides | 0.3 | 0.4 |
| Glucosylceramides | 11.5 | 12.9 |

TABLE I-continued

| Component | Batch 1 | Batch 2 |
|---|---|---|
| Lactosylceramides | 0.8 | 0.5 |
| Sphingomyelins | 36.6 | 30.7 |
| Dihydrosphingomyelins | 2.3 | 2.6 |
| Ganglioside (GM3) | 1.2 | 0.6 |
| Ganglioside (GM1) | 5.0 | 12.1 |
| Ganglioside (GM2) | 0.4 | 0 |
| Ganglioside (GD1) | 33.4 | 29.6 |
| Sulfatides | 4.0 | 6.4 |
| Phospholipids and triacylglycerides | 0.6 | 0.7 |
| Total | 100.0 | 100.0 |

The extract obtained with the process of the invention has the content by product groups as shown in Table II:

TABLE II

| Component | % |
|---|---|
| Sphingomyelins and dihydrosphingomyelins | 30-43 |
| Gangliosides | 36-46 |
| Total ceramides | 13-19 |
| Sulfatides | 2-8 |
| Phospholipids and triacylglycerides | <1 |

It can be observed that the extract of the invention has a high content of sphingomyelins, gangliosides and ceramides and low content of sulfatides. The presence of phospholipids and triacylglycerides is significantly low.

Example 2: Process for Preparing the Extract with Enzymatic Saponification

The process described in Example 1 was substantially repeated, but the saponification step was carried out by using the enzyme Lecitase Ultra (Novozymes), instead of using potassium hydroxide.

The solid fraction S2 was resuspended in water in a proportion of 1/60 (w/v) solid/water. The pH was readjusted to 6 and it was heated to 55° C., and thereby a homogeneous suspension was obtained. The enzyme Lecitase Ultra was added to this suspension under stirring, at a rate of 0.2 L of enzyme per kg of the solid fraction S2.

The suspension was kept under stirring and at the temperature of 55° C. for 6 h. The pH was controlled in order to maintain it at a value of 6. After the 6 h, the suspension was heated to 75° C. and maintained at this temperature for one hour. Subsequently, the pH was lowered to 2 by addition of hydrochloric acid.

The product was precipitated over 4 volumes of acetone relative to the initial volume. It was decanted and the supernatant, containing the fatty acids from the saponification of the extract, was removed.

About 3 volumes of acetone were added over the solid and stirred for at least 30 min. It was decanted and the supernatant was removed. The solid fraction S3 was obtained.

The product was drained and dried under vacuum at a temperature of approximately 60° C.

An extract was obtained with a composition substantially analogous to that of Example 1, except that the content of phospholipids and triacylglycerides is higher, as shown in Table III:

TABLE III

| Component | % |
|---|---|
| Sphingomyelins and dihydrosphingomyelins | 28-41 |
| Gangliosides | 34-44 |
| Total ceramides | 12-18 |
| Sulfatides | 2-7 |
| Phospholipids and triacylglycerides | <6 |

Example 3: Assay of the Brain Extract in a Mouse Model

The brain extract of the invention was subjected to several tests using a mouse model with the purpose of determining its protective effect in relation to neurodegenerative diseases, using to this end the responses derived from animal behaviour and the analysis of biochemical markers derived from the toxicity of β-amyloid peptide (lipid peroxidation and levels of proinflammatory cytokines).

A) Study of Variations in Behaviour and Neuroprotective Activity Against Lipid Peroxidation Compounds and Extracts In this study a brain extract obtained according to the process described in Example 1 was used, solubilised in bidistilled water.

A concentrated extract of DHA and EPA was also used, containing 50% by weight of DHA and 20% by weight of EPA in the form of triglycerides, solubilised in sesame oil. In the control groups sesame oil was used as vehicle.

The β-amyloid peptide, Aβ25-35, CAS Registry No. 131602-53-4, and the scrambled-β-amyloid peptide, Sc.Aβ, were obtained from the company Polypeptides (France).

Animals 116 male Swiss mice, 5 weeks old, and weighing from 30 to 35 g were used, obtained from the company Janvier (France). The animals of each group were housed in separate cages with free access to food and water except during the behavioural experiments.

Treatment Groups

With the 116 animals 11 groups were constituted, as shown in TABLE IV:

TABLE IV

| Group | Treatment | Dose (mg/kg oral) | Nr. of animals |
|---|---|---|---|
| 1 | Sc.Aβ + vehicle | — | 12 |
| 2 | Aβ$_{25-35}$ + vehicle | — | 12 |
| 3 | Aβ$_{25-35}$ + extract Example 1 | 100 | 4 |
| 4 | Aβ$_{25-35}$ + extract Example 1 | 200 | 12 |
| 5 | Aβ$_{25-35}$ + extract Example 1 | 500 | 12 |
| 6 | Aβ$_{25-35}$ + extract Example 1 | 1000 | 4 |
| 7 | Aβ$_{25-35}$ + extract DHA/EPA | 300 | 12 |
| 8 | Aβ$_{25-35}$ + extract DHA/EPA | 450 | 12 |
| 9 | Aβ$_{25-35}$ + extract DHA/EPA | 600 | 12 |
| 10 | Aβ$_{25-35}$ + extract Example 1 + extract DHA/EPA | 100 + 300 | 12 |
| 11 | Aβ$_{25-35}$ + extract Example 1 + extract DHA/EPA | 100 + 450 | 12 |
| Total | | | 116 |

Between day 1 and day 17, the extracts were administered orally by oral gavage once a day.

At day 8, amyloid peptide Sc.Aβ or oligomeric amyloid peptide Aβ$_{25-35}$ were injected intracerebroventricularly (ICV) to provoke toxicity associated to the β-amyloid peptide. The preparation of the peptides and the injection thereof were performed according to the method described in Maurice et al., *Amnesia induced in mice by centrally administered beta-amyloid peptides involves cholinergic dysfunction*, Brain Res., 1996, 706(2), 181-93.

At day 15 (7 days after peptide injection) the spontaneous alternation test in the Y-maze was carried out, to assess the spatial working memory.

At day 17 the passive avoidance test was carried out, to assess contextual long-term memory, with training at day 16 and retention session at day 17.

On day 17, after the passive avoidance test session, animals were sacrificed. Blood samples of each animal were collected. The hippocampus and frontal cortex were dissected out, frozen in liquid nitrogen and then stored at −80° C.

The hippocampi were used to determine the lipid peroxidation levels by means of a colorimetric method, using from 2 to 6 animals per group.

The other brain structures were kept at −80° C. during 3 months for possible supplementary biochemical assays.

Spontaneous Alternation Test

On day 7, all animals were tested for spontaneous alternation performance in the Y-maze, an index of spatial working memory.

The Y-maze was made of grey PVC. Each arm was 40 cm long, 13 cm high, 3 cm wide at the bottom and 10 cm wide at the top, and they converged at an equal angle. Each animal was placed at the end of one arm and was allowed to move freely through the maze during 8 min. The arm entries, including possible returns into the same arm, were checked visually. An alternation was defined as an entry into all three arms on consecutive occasions. The maximum number of alternations is therefore the total number of arm entries minus 2, and the percentage of alternation was calculated as (No of actual alternations/maximum No of alternations)×100. Parameters included the percentage of alternation (memory index) and total number of arm entries (exploration index), as described in Maurice et al., op. cit., and Meunier et al., *The anti-amnesic and neuroprotective effects of donepezil against amyloid beta25-35 peptide-induced toxicity in mice involve an interaction with the sigma 1 receptor*, Br. J. Pharmacol., 2006, 149(8), 998-1012.

Animals showing an extreme behavior (alternation percentage <20% or >90% or number of arm entries <10) were discarded from the calculation. Only one animal was discarded.

Passive Avoidance Test

The apparatus used to perform this test consisted in a two-compartment (15×20×15 cm height) box, one illuminated with white PVC walls, and the other darkened with black PVC walls and a grid floor. A guillotine door separated the two compartments. Electric shocks (0.3 mA for 3 s) were delivered to the grid floor using a shock generator (Lafayette Instruments, USA). The guillotine door was initially closed during the training session. During this session, each animal was placed into the white compartment. After 5 s, the door was raised. When the animal entered the black compartment and placed its paws on the grid floor, the door was closed and an electric shock was delivered during 3 s. The step-through latency, that is, the latency spent to enter the dark compartment, and the number of vocalizations were recorded. The retention test was carried out 24 h after training. Each animal was placed into the white compartment. After 5 s, the door was raised. The step-through and escape latencies (corresponding to the re-entry from the dark compartment) were recorded up to 300 s, as described in Meunier et al., op. cit.

In this type of testing, animals showing latencies lower than 10 s during the training session and during the retention session are considered as failing to respond to the test and are discarded from the calculations. In this study, no animal was discarded.

Determination of Lipid Peroxidation

At day 17, all the animals from each group were sacrificed and both hippocampi were rapidly removed. They were weighed and kept in liquid nitrogen until assayed. After thawing, one hippocampus per animal was homogenized in cold methanol (1/10 w/v), centrifuged at 1000 g during 5 min and the supernatant was placed in an Eppendorf tube. To each tube were added $FeSO_4$ 1 mM, $H_2SO_4$ 0.25 M, xylenol orange 1 mM, and was incubated for 30 min at room temperature. After recording the absorbance at 580 nm (A580_1), 10 μl of cumene hydroperoxide (CHP) 1 mM were added to the sample and incubated for 30 min at room temperature to determine the maximum oxidation level. The absorbance was recorded at 580 nm (A580_2). The level of lipid peroxidation was calculated as CHP equivalents according to the equation:

$$CHPE = (A508\_1/A508\_2) \times [CHP] \text{ expressed in nmol,}$$

and expressed as CHP equivalents per mg of tissue and as percentage of control group data (animals treated with Sc.Aβ and vehicle).

Statistical Analysis

All values, except passive avoidance latencies, were expressed as mean±standard error of the mean (SEM). Analyses were performed separately for each compound using one-way ANOVA (F value), followed by the Dunnett's post-hoc multiple comparison test. Passive avoidance latencies do not follow a Gaussian distribution, and were analyzed using a Kruskal-Wallis non-parametric ANOVA, followed by Dunn's multiple comparison test.

Results

In TABLE V (FIG. 2.1) the results corresponding to the spontaneous alternation in the Y-maze test are shown, expressed as mean value of the percentage of alternation and standard error of the mean:

TABLE V

| Group | Treatment | Dose (mg/kg oral) | Alternation (%) |
|---|---|---|---|
| 1 | Sc.Aβ + vehicle | — | 71.8 (1.7) |
| 2 | Aβ$_{25-35}$ + vehicle | — | 53.2 (2.9) |
| 3 | Aβ$_{25-35}$ + extract Example 1 | 100 | 55.7 (2.1) |
| 4 | Aβ$_{25-35}$ + extract Example 1 | 200 | 73.2 (2.6) |
| 5 | Aβ$_{25-35}$ + extract Example 1 | 500 | 72.3 (1.8) |
| 6 | Aβ$_{25-35}$ + extract Example 1 | 1000 | 73.1 (1.9) |
| 7 | Aβ$_{25-35}$ + extract DHA/EPA | 300 | 51.5 (2.4) |
| 8 | Aβ$_{25-35}$ + extract DHA/EPA | 450 | 64.9 (1.7) |
| 9 | Aβ$_{25-35}$ + extract DHA/EPA | 600 | 75.0 (1.8) |
| 10 | Aβ$_{25-35}$ + extract Example 1 + extract DHA/EPA | 100 + 300 | 52.0 (1.9) |
| 11 | Aβ$_{25-35}$ + extract Example 1 + extract DHA/EPA | 100 + 450 | 76.6 (1.3) |

It can be observed that:

The extract of the invention effectively prevents the spatial working memory deficits induced by Aβ$_{25-35}$ peptide toxicity, from a dose of 200 mg/kg (Groups 4-6).

In TABLE VI (FIG. 2.2) the results corresponding to the spontaneous alternation in the Y-maze test are shown, expressed as mean of groups 2, 3, 8 and 11 relative to the control group (group 1):

TABLE VI

| Group | Treatment | Dose (mg/kg oral) | Difference from group 1 |
|---|---|---|---|
| 1 | Sc.Aβ + vehicle | — | 0 |
| 2 | Aβ$_{25-35}$ + vehicle | — | −18.6 |
| 3 | Aβ$_{25-35}$ + extract Example 1 | 100 | −16.1 |
| 8 | Aβ$_{25-35}$ + extract DHA/EPA | 450 | −6.9 |
| 11 | Aβ$_{25-35}$ + extract Example 1 + extract DHA/EPA | 100 + 450 | +5.2 |

The results of the groups 2, 3, 8 and 11 can be viewed as a factorial design $2^2$ according to TABLE VII of factors (Extract of the invention and Extract DHA/EPA) and results:

TABLE VII

| Test | Extract of the invention (mg/kg) | Extract DHA/EPA (mg/kg) | Difference relative to group 1 |
|---|---|---|---|
| 2 | No | No | −18.6 |
| 3 | Yes (100) | No | −16.1 |
| 8 | No | Yes (450) | −6.9 |
| 11 | Yes (100) | Yes (450) | +5.2 |

The effects calculated from the results of TABLE VI for each of the factors and their interaction are as follows:

Effect of the extract of the invention: +7.3
Effect of the extract DHA/EPA: +16.5
Effect of the interaction: +4.8

The interaction between the two extracts is statistically significant and means that the effect of the combination of both is not additive, but has a clear synergistic effect.

Thus, it can be observed that the combination of the lowest dose of the extract of the invention (100 mg/kg) with the high dose (450 mg/kg) of the extract comprising DPA and EPA has a synergistic effect, which is significantly greater than the sum of the effects of the components administered separately.

While the group treated with the lowest dose of the extract of the invention has an effect comparable to that of the group treated with vehicle and the β-amyloid peptide, Aβ$_{25-35}$) for the group treated with the extract of the invention combined with an extract comprising DHA, the effect obtained is not the simple addition of the effects of both extracts, but a higher effect is obtained.

In TABLE VIII (FIGS. 3.1 and 3.2) the results corresponding to the passive avoidance test are shown, expressed in seconds, as mean values and standard error of the mean of the step-through latency and escape latency:

TABLE VIII

| Group | Treatment | Dose (mg/kg oral) | Pass-through latency (s) | Escape latency (s) |
|---|---|---|---|---|
| 1 | Sc.Aβ + vehicle | — | 229.8 (20.0) | 25.8 (4.6) |
| 2 | Aβ$_{25-35}$ + vehicle | — | 105.8 (14.2) | 62.3 (7.1) |
| 3 | Aβ$_{25-35}$ + extract Example 1 | 100 | 151.7 (17.8) | 51.0 (3.8) |
| 4 | Aβ$_{25-35}$ + extract Example 1 | 200 | 195.2 (19.9) | 34.3 (5.2) |
| 5 | Aβ$_{25-35}$ + extract Example 1 | 500 | 250.3 (15.8) | 22.1 (3.0) |
| 6 | Aβ$_{25-35}$ + extract Example 1 | 1000 | 253.4 (10.9) | 22.1 (2.0) |
| 7 | Aβ$_{25-35}$ + extract DHA/EPA | 300 | 88.8 (8.9) | 57.0 (5.6) |
| 8 | Aβ$_{25-35}$ + extract | 450 | 193.3 (13.6) | 29.5 (3.8) |

TABLE VIII-continued

| Group | Treatment | Dose (mg/kg oral) | Pass-through latency (s) | Escape latency (s) |
|---|---|---|---|---|
| | DHA/EPA | | | |
| 9 | Aβ$_{25-35}$ + extract DHA/EPA | 600 | 249.8 (15.2) | 14.5 (2.5) |
| 10 | Aβ$_{25-35}$ + extract Example 1 + extract DHA/EPA | 100 + 300 | 117.3 (9.7) | 51.9 (4.1) |
| 11 | Aβ$_{25-35}$ + extract Example 1 + extract DHA/EPA | 100 + 450 | 263.7 (12.5) | 18.2 (2.0) |

It can be observed that the extract of the invention effectively prevents the long term memory deficits induced Aβ$_{25-35}$ peptide toxicity, from a dose of 200 mg/kg (Groups 4-6), and particularly from 500 mg/kg.

In TABLE IX (FIG. 4) the results corresponding to the lipid peroxidation test are shown, expressed as the mean value and standard error of the mean of the CHP equivalents per weight of wet tissue (ECHP):

TABLE IX

| Group | Treatment | Dose (mg/kg oral) | ECHP |
|---|---|---|---|
| 1 | Sc.Aβ + vehicle | — | 1926 (75) |
| 2 | Aβ$_{25-35}$ + vehicle | — | 3626 (147) |
| 3 | Aβ$_{25-35}$ + extract Example 1 | 100 | 2772 (182) |
| 4 | Aβ$_{25-35}$ + extract Example 1 | 200 | 2787 (152) |
| 5 | Aβ$_{25-35}$ + extract Example 1 | 500 | 1993 (80) |
| 6 | Aβ$_{25-35}$ + extract Example 1 | 1000 | 2002 (98) |
| 7 | Aβ$_{25-35}$ + extract DHA/EPA | 300 | 3536 (146) |
| 8 | Aβ$_{25-35}$ + extract DHA/EPA | 450 | 2886 (203) |
| 9 | Aβ$_{25-35}$ + extract DHA/EPA | 600 | 2201 (146) |
| 10 | Aβ$_{25-35}$ + extract Example 1 + extract DHA/EPA | 100 + 300 | 2763 (143) |
| 11 | Aβ$_{25-35}$ + extract Example 1 + extract DHA/EPA | 100 + 450 | 1960 (102) |

It can be observed that the extract of the invention has neuroprotective activity in the reduction of the levels of lipid peroxidation, a consequence of oxidative stress, from a dose of 100 mg/kg. A complete blockage is observed from a dose of 500 mg/kg (Groups 5 and 6).

B) Study of the Neuroprotective Activity Related to Proinflammatory Cytokines

Compounds and Extracts

In this study the brain extract obtained according to the process described in Example 1 was used, solubilised in bidistilled water.

In control groups sesame oil was used as vehicle.

The β-amyloid peptide, Aβ$_{25-35}$, CAS Registry No. 131602-53-4, and the scrambled-β-amyloid peptide, Sc.Aβ, were obtained from the company Polypeptides (France).

Animals 72 male Swiss mice, 5 weeks old and weighing from 30 to 35 g were used, obtained from the company Janvier (France). The animals of each group were housed in separate cages with free access to food and water, except during the behavioural experiments.

Treatment Groups

With the 72 animals, 6 groups of 12 animals each were constituted, as shown in TABLE X:

TABLE X

| Group | Treatment | Dose (mg/kg oral) | Weeks of treatment |
|---|---|---|---|
| 1 | Sc.Aβ + vehicle | — | — |
| 2 | Aβ$_{25-35}$ + vehicle | — | — |
| 3 | Aβ$_{25-35}$ + extract Example 1 | 100 | 2 |
| 4 | Aβ$_{25-35}$ + extract Example 1 | 1000 | 2 |
| 5 | Aβ$_{25-35}$ + extract Example 1 | 100 | 4 |
| 6 | Aβ$_{25-35}$ + extract Example 1 | 1000 | 4 |

Between day 1 and day 31 (for groups 1, 2, 5 and 6) or between day 15 and day 31 (for groups 3 and 4) the extracts were administered orally by oral gavage once a day.

At day 22 amyloid peptide Sc.Aβ or oligomeric amyloid peptide Aβ$_{25-35}$ were injected intracerebroventricularly (ICV) to provoke toxicity associated to the β-amyloid peptide. The preparation of the peptides and the injection thereof were performed according to the method described in Maurice et al., op. cit.

At day 31 animals were sacrificed. Blood samples were collected from each animal. The hippocampus and frontal cortex were dissected out and were frozen with liquid nitrogen and kept at a temperature of −80° C. In 6 animals per group the hippocampi were used to determine by ELISA the levels of the proinflammatory cytokines interleukin-1β (IL1β), interleukin-6 (IL6) and tumor necrosis factor α (TNFα).

ELISA Assays

The following commercial kits were used:
  IL1β: Reference SEA563Mu (USCN Life Science)
  IL6: Reference SEA079Mu (USCN Life Science)
  TNFα: Reference EMTNFA01 (ThermoScientific)

The hippocampi were prepared and assayed in duplicate according to the following process: the hippocampi were homogenized after thawing in a 50 mM Tris and 150 mM NaCl buffer solution, at pH 7.5, and sonicated for 10 s. After centrifugation at 5000 g for 10 minutes at 4° C., supernatants were used for ELISA assays according to the manufacturer's instructions. In each assay the absorbance at 450 nm was recorded, and sample concentration was calculated using a calibration curve. The results were expressed as pg of marker per ml of supernatant.

Statistical Analysis

All values were expressed as mean±standard error of the mean (SEM). Analyses were performed for each treatment using one-way ANOVA (F value), followed by the Dunnett's post-hoc multiple comparison test.

Results

In TABLE XI (FIG. 5) the results obtained for the three proinflammatory cytokines are shown, expressed in pg/ml (mean value and standard error of the mean):

TABLE XI

| Group | Treatment | Dose (mg/kg oral) | Weeks | IL1β (pg/ml) | IL6 (pg/ml) | TNFα (pg/ml) |
|---|---|---|---|---|---|---|
| 1 | Sc.Aβ+ vehicle | — | — | 69.5 (1.7) | 109.1 (1.2) | 436.8 (9.0) |
| 2 | Aβ$_{25-35}$ + vehicle | — | — | 93.7 (1.1) | 127.8 (1.7) | 633.6 (24.0) |
| 3 | Aβ$_{25-35}$ + extract Example 1 | 100 | 2 | 86.1 (2.3) | 129.2 (1.8) | 560.6 (29.9) |
| 4 | Aβ$_{25-35}$ + extract Example 1 | 1000 | 2 | 79.4 (3.6) | 109.7 (1.3) | 457.5 (18.0) |
| 5 | Aβ$_{25-35}$ + extract Example 1 | 100 | 4 | 78.5 (3.4) | 110.3 (1.3) | 436.3 (16.4) |

TABLE XI-continued

| Group | Treatment | Dose (mg/kg oral) | Weeks | IL1ß (pg/ml) | IL6 (pg/ml) | TNFα (pg/ml) |
|---|---|---|---|---|---|---|
| 6 | Aβ$_{25-35}$ + extract Example 1 | 1000 | 4 | 74.8 (3.4) | 110.3 (1.7) | 450.3 (13.8) |

In FIG. 5 the results are presented so that the value of the control group 1 is assigned to 100, and other groups refer to that value.

It can be observed that:

Injection of Aβ$_{25-35}$ peptide highly significantly increased inflammation in the hippocampus of animals compared to animals treated with scrambled-β-amyloid peptide, Sc.Aβ.

The extract of the invention has an antiinflammatory effect, which may be related with a neuroprotective activity against the inflammatory cytokines induced by the Aβ$_{25-35}$ peptide. In particular, the effect is more significant when the dose is 100 mg/kg for 4 weeks, or 1000 mg/kg for 2 weeks.

The invention claimed is:

1. A process for preparing an animal brain extract, comprising:
   1) subjecting minced brains to an extraction with a mixture of ethanol:water or with a mixture of chloroform:methanol and separating the liquid fraction, referred to as L1,
   2) distilling the solvent of the liquid fraction L1, and precipitating with acetone to obtain the solid fraction, referred to as S2,
   3) saponifying the solid fraction S2, discarding the products soluble in acetone resulting from the saponification, and obtaining the solid fraction, referred to as S3.

2. The process according to claim 1, wherein the brain is of porcine origin.

3. The process according to claim 1, wherein the ethanol:water mixture is in a ratio of between 80:20 and 60:40 expressed in (v/v).

4. The process according to claim 1, wherein the chloroform:methanol mixture is in a ratio of between 70:30 and 60:40 expressed in (v/v).

5. The process according to claim 1, further comprising a step of degreasing of the brains by extraction with a solvent selected from acetone, hexane and carbonic anhydride in supercritical conditions before step 1).

6. The process according to claim 1, wherein the saponification is carried out by treatment with an aqueous solution of an alkali hydroxide.

7. The process according to claim 6, further comprising a step of washing the solid fraction S3.

8. The process according to claim 1, further comprising a step of drying the solid fraction S3.

9. A brain extract obtained by a process for preparing an animal brain extract, the process comprising:
   1) subjecting minced brains to an extraction with a mixture of ethanol:water or with a mixture of chloroform:methanol and separating the liquid fraction, referred to as L1,
   2) distilling the solvent of the liquid fraction L1, and precipitating with acetone to obtain the solid fraction, referred to as S2, and
   3) saponifying the solid fraction S2, discarding the products soluble in acetone resulting from the saponification, and obtaining the solid fraction, referred to as S3.

10. The brain extract according to claim 9, wherein the content of sphingomyelins is comprised between 28% and 43% by weight relative to the total weight of the extract, the content of gangliosides is comprised between 34% and 46% by weight relative to the total weight of the extract, the content of ceramides is comprised between 12% and 19% by weight relative to the total weight of the extract, the content of sulfatides is comprised between 2% and 8% by weight relative to the total weight of the extract, and the content of phospholipids and triacylglycerides is lower than 10%, and the sum of the percentages of the components of the extract is the 100%.

11. A composition comprising the brain extract of claim 9 and at least one vehicle or excipient.

12. The composition according to claim 11, further comprising at least one additional active component suitable for the prevention and/or treatment of neurodegenerative and/or central nervous system diseases, or to support the health of the nervous system.

13. The composition according to claim 12, wherein the additional active component comprises an extract of omega-3 acids in the form of triglycerides.

14. The brain extract of claim 9 adapted for use as medicament.

15. A pharmaceutical composition comprising the brain extract of claim 9.

16. The brain extract according to claim 9, wherein the brain is of porcine origin.

17. The brain extract according to claim 9, wherein the ethanol:water mixture is in a ratio comprised between 80:20 and 60:40 expressed in (v/v).

18. The brain extract according to claim 9, wherein the chloroform:methanol mixture is in a ratio comprised between 70:30 and 60:40 expressed in (v/v).

19. The brain extract according to claim 9, wherein the process further comprises degreasing the brains by extraction with a solvent selected from acetone, hexane and carbonic anhydride in supercritical conditions.

20. The brain extract according to claim 9, wherein the saponification is carried out by treatment with an aqueous solution of an alkali hydroxide.

21. The brain extract according to claim 20, wherein the process further comprises washing the solid fraction S3.

22. The brain extract according to claim 9, wherein the process further comprises drying the solid fraction S3.

* * * * *